(12) United States Patent
Ogura (10) Patent No.: US 6,338,718 B1
(45) Date of Patent: Jan. 15, 2002

(54) SUPERIOR-AND-INFERIOR-LIMB BLOOD-PRESSURE INDEX MEASURING APPARATUS

(75) Inventor: Toshihiko Ogura, Inuyama (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/558,549

(22) Filed: Apr. 26, 2000

(30) Foreign Application Priority Data

May 7, 1999 (JP) ............................................ 11-126861

(51) Int. Cl.⁷ ................................................. A61B 5/02
(52) U.S. Cl. ........................ 600/490; 600/485; 600/500
(58) Field of Search .................................. 600/481, 485, 600/490, 492–495, 499–502

(56) References Cited

U.S. PATENT DOCUMENTS

| 4,669,485 A | * | 6/1987 | Russell ........................ 600/492 |
| 5,836,888 A | | 11/1998 | Ogura et al. |
| 6,228,033 B1 | * | 5/2001 | Koobi et al. ................. 600/483 |

FOREIGN PATENT DOCUMENTS

| EP | 0 885 588 A | 12/1998 |
| GB | 2 281 782 A | 3/1995 |
| JP | 03 162827 | 7/1991 |
| NL | 1003125 | 6/1997 |

* cited by examiner

Primary Examiner—John P. Lacyk
Assistant Examiner—Ryan Carter
(74) Attorney, Agent, or Firm—Oliff & Berridge, PLC (57) ABSTRACT

An apparatus for measuring a superior-and-inferior-limb blood-pressure index of a living subject, including a first blood-pressure measuring device which measures a first blood pressure of an inferior limb of the subject, a second blood-pressure measuring device which measures a second blood pressure of a superior limb of the subject, an index determining device for determining the superior-and-inferior-limb blood-pressure index, based on the first blood pressure measured by the first blood-pressure measuring device and the second blood pressure measured by the second blood-pressure measuring device, a time-information storing device which stores first time information representing a first time when the first blood pressure is measured by the first blood-pressure measuring device, and second time information representing a second time when the second blood pressure is measured by the second blood-pressure measuring device, and a time-information displaying device which displays, in a graph having at least a time-information axis representing time information, a first symbol representing the first time information stored in the time-information storing device, and a second symbol representing the second time information stored in the time-information storing device, along the time-information axis, so that an observer can compare the first and second symbols with each other.

10 Claims, 6 Drawing Sheets

SUPERIOR-AND-INFERIOR-LIMB BLOOD-PRESSURE INDEX MEASURING APPARATUS

BACKGROUND OF THE INVENTION

1. Field of the Invention

The present invention relates to an apparatus for measuring a superior-and-inferior-limb blood-pressure index of a living subject (e.g., a ratio of an inferior-limb blood pressure to a superior-limb blood pressure, or a ratio of a superior-limb blood pressure to an inferior-limb blood pressure), and particularly to the art of evaluating the measured superior-and-inferior-limb blood-pressure index.

2. Related Art Statement

Arteriosclerotic cardiovascular disease is one of major death causes of aged women, e.g., not younger than sixty five years, but there is no general method of finding latent arteriosclerosis. However, it is known that since measuring superior-and-inferior-limb blood-pressure index can be used as a simple and repeatable method to find inferior-limb arterial disease and can be used to check quickly and easily the condition of whole cardiovascular system, the index is useful to identify individuals who need special treatments to reduce its death rate or its incidence rate.

Generally, the above superior-and-inferior-limb blood-pressure index (hereinafter, abbreviated to the "SIL BP index") is obtained or calculated as the ratio of a systolic blood pressure ("BP") of an ankle as the inferior-limb BP to a systolic BP of an upper arm as the superior-limb BP, that is, ankle/arm BP index (abbreviated to "API" or "ABI"). If the measured ankle/arm BP index of a living person is smaller than a threshold, e.g., about 0.9, abnormality may be diagnosed on the person. Thus, even a small change of the systolic BP of the inferior or superior limb greatly affects the diagnosis.

The BP of a living person can change in a short time. For example, the BP of a living person at rest can physiologically change by more than 20 mmHg in ten seconds. Therefore, if there is a time difference between a first time when a systolic BP is measured from an inferior limb and a second time when a systolic BP is measured from a superior limb, the BP of the person may change during the time difference. However, a conventional SIL BP index measuring device does not enable an observer to recognize easily a time difference between a first time when a systolic BP is measured from an inferior limb and a second time when a systolic BP is measured from a superior limb.

SUMMARY OF THE INVENTION

It is therefore an object of the present invention to provide a superior-and-inferior-limb blood-pressure ("SIL BP") index measuring apparatus which enables an observer to recognize easily a time difference between a first time when a systolic BP is measured from an inferior limb and a second time when a systolic BP is measured from a superior limb.

(1) According to a first feature of the present invention, there is provided an apparatus for measuring a superior-and-inferior-limb blood-pressure index of a living subject, comprising a first blood-pressure measuring device which measures a first blood pressure of an inferior limb of the subject; a second blood-pressure measuring device which measures a second blood pressure of a superior limb of the subject; index determining means for determining the superior-and-inferior-limb blood-pressure index, based on the first blood pressure measured by the first blood-pressure measuring device and the second blood pressure measured by the second blood-pressure measuring device; a time-information storing device which stores first time information representing a first time when the first blood pressure is measured by the first blood-pressure measuring device, and second time information representing a second time when the second blood pressure is measured by the second blood-pressure measuring device; and a time-information displaying device which displays, in a graph having at least a time-information axis representing time information, a first symbol representing the first time information stored in the time-information storing device, and a second symbol representing the second time information stored in the time-information storing device, along the time-information axis, so that an observer can compare the first and second symbols with each other.

According to this feature, the time-information displaying device displays, in the graph having at least the time-information axis representing the time information, the first symbol representing the first time information stored in the time-information storing device, and the second symbol representing the second time information stored in the time-information storing device, along the time-information axis, so that the observer can compare the first and second symbols with each other. Therefore, the observer can easily recognize visually a difference between the first and second times represented by the first and second symbols.

(2) According to a second feature of the present invention that includes the first feature (1), the time-information storing device comprises a memory which temporarily stores the first time information and the second time information.

(3) According to a third feature of the present invention that includes the second feature (2), the memory comprises a random access memory.

(4) According to a fourth feature of the present invention that includes any one of the first to third features (1) to (3), the apparatus further comprises an operable device which is operable by an operator and which outputs a symbol-move signal representing an amount of operation thereof; and symbol moving means for moving, based on the symbol-move signal supplied from the operable device, one of the first and second symbols relative to the other of the first and second symbols, along the time-information axis of the graph. According to this feature, the operator can move, by operating the operable device, one of the first and second symbols relative to the other of the first and second symbols, along the time-information axis of the graph, so that the first and second symbols coincide with each other in the graph. Based on the amount of operation of the operable device to move one of the first and second symbols relative to the other of the first and second symbols till the first and second symbols coincide with each other, the operator can easily recognize a difference between the first and second times represented by the first and second symbols.

(5) According to a fifth feature of the present invention that includes any one of the first to fourth features (1) to (4), the index determining means comprises means for determining, as the superior-and-inferior-limb blood-pressure index, a ratio of the first blood pressure to the second blood pressure, or a ratio of the second blood pressure to the first blood pressure.

(6) According to a sixth feature of the present invention, there is provided an apparatus for measuring a superior-and-inferior-limb blood-pressure index of a living subject, comprising a first blood-pressure measuring device which includes a first inflatable cuff which is adapted to be wound around an inferior limb of the subject, and a first pulse-wave sensor which detects each of a plurality of heartbeat-synchronous pulses of a first pulse wave produced from a first artery pressed by the first cuff, the first blood-pressure measuring device measuring a first blood pressure of the inferior limb of the subject; a second blood-pressure measuring device which includes a second inflatable cuff which is adapted to be wound around a superior limb of the subject, and a second pulse-wave sensor which detects each of a plurality of heartbeat-synchronous pulses of a second pulse wave produced from a second artery pressed by the second cuff, the second blood-pressure measuring device measuring a second blood pressure of the superior limb of the subject; index determining means for determining the superior-and-inferior-limb blood-pressure index, based on the first blood pressure measured by the first blood-pressure measuring device and the second blood pressure measured by the second blood-pressure measuring device; a peak-magnitude and time-information storing device which stores a first magnitude of a peak of each of the heartbeat-synchronous pulses of the first pulse wave detected by the first pulse-wave sensor, and a first time information representing a first time when the each pulse of the first pulse wave is detected by the first pulse-wave sensor, and stores a second magnitude of a peak of each of the heartbeat-synchronous pulses of the second pulse wave detected by the second pulse-wave sensor, and a second time information representing a second time when the each pulse of the second pulse wave is detected by the second pulse-wave sensor; a distribution displaying device which displays, in a first two-dimensional graph having a time-information axis representing time information and a first-peak-magnitude axis representing first peak magnitude, a distribution of the respective first peak magnitudes of the heartbeat-synchronous pulses of the first pulse wave, stored in the peak-magnitude and time-information storing device, along the time-information axis, and additionally displays, in a second two-dimensional graph which has the time-information axis and a second-peak-magnitude axis representing second peak magnitude, a distribution of the respective second peak magnitudes of the heartbeat-synchronous pulses of the second pulse wave, stored in the peak-magnitude and time-information storing device, along the time-information axis; and a time-information displaying device which displays, along the time-information axis of the first two-dimensional graph in which the first distribution is displaced, a first symbol representing the first time information which is stored in the peak-magnitude and time-information storing device and which represents the first time when the first blood pressure is measured by the first blood-pressure measuring device, and additionally displays, along the time-information axis of the second two-dimensional graph in which the second distribution is displaced, a second symbol representing the second time information which is stored in the peak-magnitude and time-information storing device and which represents the second time when the second blood pressure is measured by the second blood-pressure measuring device.

According to this feature, the peak-magnitude and time-information storing device stores a first magnitude of a peak of each of the heartbeat-synchronous pulses of the first pulse wave detected by the first pulse-wave sensor, and a first time information representing a first time when the each pulse of the first pulse wave is detected by the first pulse-wave sensor, and additionally stores a second magnitude of a peak of each of the heartbeat-synchronous pulses of the second pulse wave detected by the second pulse-wave sensor, and a second time information representing a second time when the each pulse of the second pulse wave is detected by the second pulse-wave sensor. The distribution displaying device displays, in a first two-dimensional graph having a time-information axis representing time information and a first-peak-magnitude axis representing first peak magnitude, a distribution of the respective first peak magnitudes of the heartbeat-synchronous pulses of the first pulse wave, stored in the peak-magnitude and time-information storing device, along the time-information axis, and additionally displays, in a second two-dimensional graph which has the time-information axis and a second-peak-magnitude axis representing second peak magnitude, a distribution of the respective second peak magnitudes of the heartbeat-synchronous pulses of the second pulse wave, stored in the peak-magnitude and time-information storing device, along the time-information axis, and the time-information displaying device displays a first symbol representing the first time information, and a second symbol representing the second time information. Therefore, an observer can easily recognize visually a difference between the first and second times represented by the first and second symbols.

(7) According to a seventh feature of the present invention that includes the sixth feature (6), the peak-magnitude and time-information storing device comprises a memory which temporarily stores the respective first peak magnitudes of the heartbeat-synchronous pulses of the first pulse wave, the respective first time information representing the respective first times when the respective heartbeat-synchronous pulses of the first pulse wave are detected by the first pulse-wave sensor, the respective second peak magnitudes of the heartbeat-synchronous pulses of the second pulse wave, and the respective second time information representing the respective second times when the respective heartbeat-synchronous pulses of the second pulse wave are detected by the second pulse-wave sensor.

(8) According to an eighth feature of the present invention that includes the seventh feature (7), the memory comprises a random access memory.

(9) According to a ninth feature of the present invention that includes any one of the sixth to eighth features (6) to (8), the apparatus further comprises an operable device which is operable by an operator and which outputs a symbol-move signal representing an amount of operation thereof; and symbol moving means for moving, based on the symbol-move signal supplied from the operable device, one of the first and second symbols relative to the other of the first and second symbols, along the time-information axis of a corresponding one of the first and second two-dimensional graphs. The present apparatus enjoys the same advantages as those of the apparatus according to the fourth feature (4).

(10) According to a tenth feature of the present invention that includes any one of the sixth to ninth features (6) to (9), the index determining means comprises means for determining, as the superior-and-inferior-limb blood-pressure index, a ratio of the first blood pressure to the second blood pressure, or a ratio of the second blood pressure to the first blood pressure.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
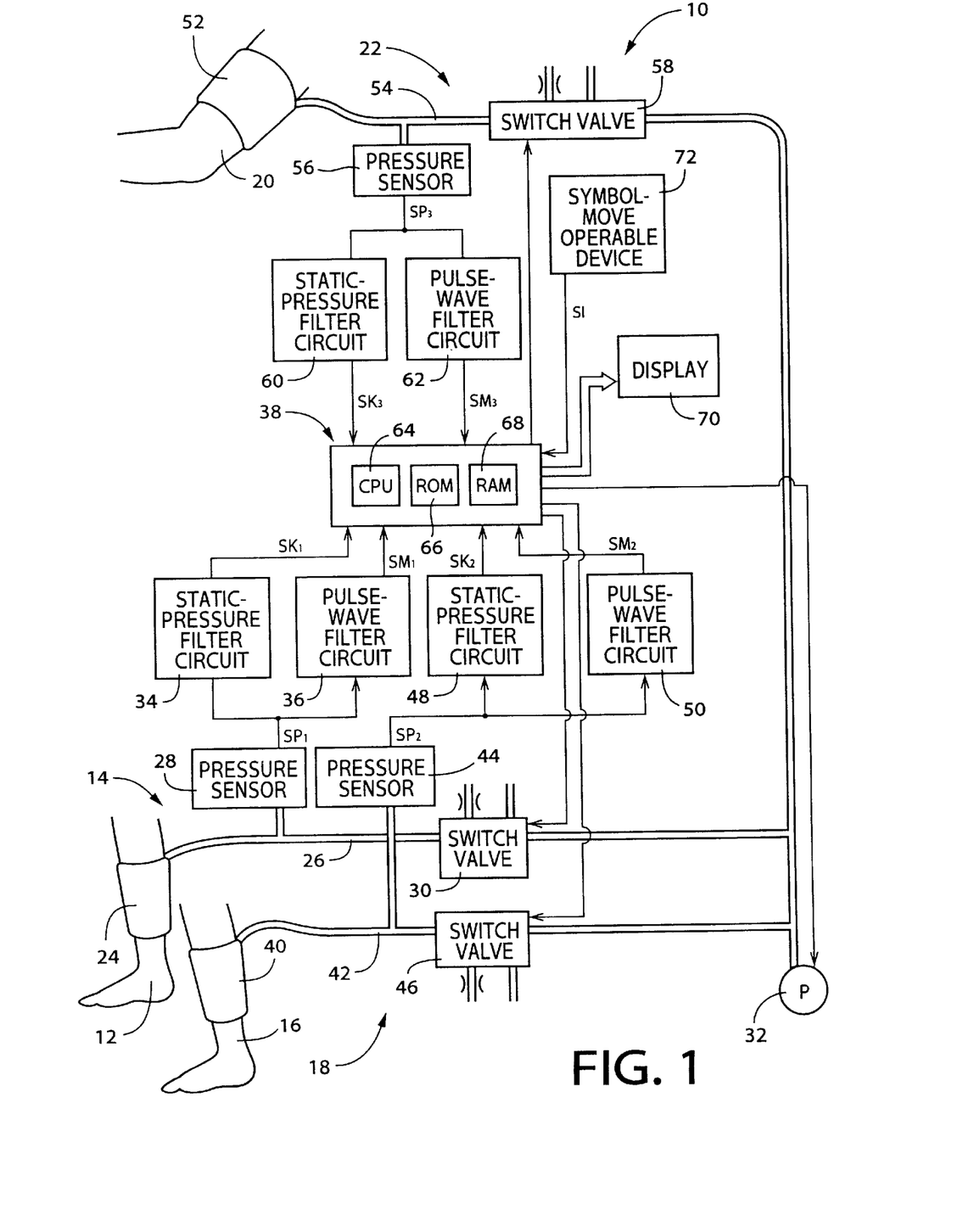
FIG. 1 is a diagrammatic view of the construction of an ankle/arm blood-pressure ("BP") index measuring apparatus to which the present invention is applied.

Hereinafter, there will be described an ankle/arm blood-pressure ("BP") index measuring apparatus 10 to which the present invention is applied, by reference to the drawings. FIG. 1 is a diagrammatic view showing the construction of the measuring apparatus 10. The ankle/arm BP index measuring apparatus 10 is a sort of superior-and-inferior-limb ("SIL") BP index measuring apparatus, since the measuring apparatus 10 measures, as an inferior-limb BP value, a BP value from an ankle of a patient as a living person and measures, as a superior-limb BP value, a BP value from an upper arm of the patient. The present apparatus 10 carries out the BP measurements on the patient who takes the face-down, lateral, or face-up position so that the upper arm and the ankle are substantially level with each other.

In FIG. 1, the ankle/arm BP index measuring apparatus 10 includes a right-leg first BP measuring device 14 which measures a BP value from a right ankle 12 of the patient, a left-leg first BP measuring device 18 which measures a BP value from a left ankle 16 of the patient, and a second BP measuring device 22 which measures a BP value from an upper arm 20 of the patient.

The right-leg first BP measuring device 14 includes an inflatable cuff 24 which includes a belt-like cloth bag and a rubber bag accommodated in the cloth bag and which is wound around the right ankle 12 of the patient; a piping 26; and a pressure sensor 28, an electrically-operated switch valve 30, and an air pump 32 which are connected to the cuff 24 via the piping 26. The switch valve 30 is selectively placed in one of three operation states, that is, (a) a pressurized-air-supply state in which the switch valve 30 allows pressurized air to be supplied from the air pump 32 to the cuff 24, (b) a slow-deflation state in which a degree of opening of the switch valve 30 is so controlled as to allow the pressurized air to be deflated slowly at an arbitrary rate from the cuff 24, and (c) a quick-deflation state in which the switch valve 30 allows the pressurized air to be deflated quickly from the cuff 24.

The pressure sensor 28 detects an air pressure in the cuff 24, and supplies a pressure signal, $SP_1$, representing the detected air pressure, to a static-pressure filter circuit 34 and a pulse-wave filter circuit 36. The static-pressure filter circuit 34 includes a low-pass filter which allows only low frequencies to pass therethrough and thereby selects, from the pressure signal $SP_1$, a cuff-pressure signal, $SK_1$, representing a cuff pressure, $P_{C1}$ as the constant component of the detected air pressure. The filter circuit 34 supplies the cuff-pressure signal $SK_1$ to an electronic control device 38 via an analog-to-digital ("A/D") converter (not shown).

The pulse-wave filter circuit 36 includes a bandpass filter, which allows only specific frequencies to pass therethrough and thereby selects, from the pressure signal $SP_1$, a pulse-wave signal, $SM_1$, representing a pulse wave as the oscillatory component of the detected air pressure. The filter circuit 36 supplies the pulse-wave signal $SM_1$ to the control device 38 via an A/D converter (not shown). The pulse-wave signal $SM_1$ represents a right-leg first pulse wave, $M1_R$, produced from an artery (i.e., a posterior tibial artery) of the right ankle 12 that is pressed by the cuff 24, and the pulse-wave filter circuit 36 functions as one of two first pulse-wave sensors.

The left-leg first BP measuring device 18 includes an inflatable cuff 40, a piping 42, a pressure sensor 44, and a switch valve 46 which have respective constructions identical with those of the counterparts 24, 26, 28, 30 of the right-leg first BP measuring device 14. The switch valve 46 is connected to the air pump 32. The pressure sensor 44 detects an air pressure in the cuff 40, and supplies a pressure signal, $SP_2$ representing the detected air pressure, to a static-pressure filter circuit 48 and a pulse-wave filter circuit 50 which have respective constructions identical with those of the counterparts 34, 36 of the right-leg first BP measuring device 14. The static-pressure filter circuit 48 selects, from the pressure signal $SP_2$, a cuff-pressure signal, $SK_2$, representing a cuff pressure, $P_{C2}$, as the constant component of the detected air pressure, and supplies the cuff-pressure signal $SK_2$ to the control device 38 via an A/D converter (not shown). The pulse-wave filter circuit 50 selects, from the pressure signal $SP_2$, a pulse-wave signal, $SM_2$, representing a pulse wave as the oscillatory component of the detected air pressure, and supplies the pulse-wave signal $SM_2$ to the control device 38 via an A/D converter (not shown). The pulse-wave signal $SM_2$ represents a left-leg first pulse wave, $M1_L$, produced from an artery (i.e., a posterior tibial artery) of the left ankle 16 that is pressed by the cuff 40, and the pulse-wave filter circuit 50 functions as the other of the two first pulse-wave sensors.

The second BP measuring device 22 includes an inflatable cuff 52 which has a construction identical with the cuff 24 or 40 and which is wound around an upper arm 20 (e.g., a right upper arm) of the patient; and a piping 54, a pressure sensor 56, and a switch valve 58 which have respective constructions identical with those of the counterparts 24, 26, 28, 30 of the right-leg first BP measuring device 14. The switch valve 58 is connected to the air pump 32. The pressure sensor 56 detects an air pressure in the cuff 52, and supplies a pressure signal, $SP_3$, representing the detected air pressure, to a static-pressure filter circuit 60 and a pulse-wave filter circuit 62 which have respective constructions identical with those of the counterparts 34, 36 of the right-leg first BP measuring device 14. The static-pressure filter circuit 60 selects, from the pressure signal $SP_3$, a cuff-pressure signal, $SK_3$, representing a cuff pressure, $P_{C3}$, as the constant component of the detected air pressure, and supplies the cuff-pressure signal $SK_3$ to the control device 38 via an A/D converter (not shown). The pulse-wave filter circuit 62 selects, from the pressure signal $SP_3$, a pulse-wave signal, $SM_3$, representing a pulse wave as the oscillatory component of the detected air pressure, and supplies the pulse-wave signal $SM_3$ to the control device 38 via an A/D converter (not shown). The pulse-wave signal $SM_3$ represents a second pulse wave, M2, produced from an artery (i.e., a brachial artery) of the upper arm 20 that is pressed by the cuff 52, and the pulse-wave filter circuit 62 functions as a second pulse-wave sensor.

The electronic control device 38 is essentially provided by a microcomputer including a central processing unit ("CPU") 64, a read only memory ("ROM") 66, a random access memory ("RAM") 68, and an input-and-output ("I/O") port (not shown), and processes input signals according to control programs pre-stored in the ROM 66, while utilizing the temporary-storage function of the RAM 68. The control device 38 outputs, from the I/O port, drive signals to the air pump 32 and the three switch valves 30, 46, 58 to control the respective operations thereof, and display signals to a display device 70 to control the contents displayed thereby.

A symbol-move operable device 72 includes a first button or member which is operable by an operator to move a symbol, displayed on the display device 70, in a leftward direction, and a second button or member which is operable by the operator to move the symbol in a rightward direction. Alternatively, the operable device 72 may employ a dial which is rotatable by an operator in opposite directions. The operable device 72 produces a symbol-move signal, SI, representing an amount of operation of each of the first and second buttons, or an amount, and a direction, of rotation of the dial, and supplies the signal SI to the control device 38. For example, each time the first or second button is pushed, the operable device 72 may produce one signal SI to move the symbol by a unit distance in a corresponding one of the leftward and rightward directions, and for a time duration when the first or second button is continuously pushed, the device 72 may continue producing signals SI to move continuously the symbol in a corresponding one of the leftward and rightward directions. Thus, the operable device 72 produces the symbol-move signal or signals SI representing the amount of operation of each of the first and second buttons, or the amount and direction of rotation of the dial.

Figure 2:
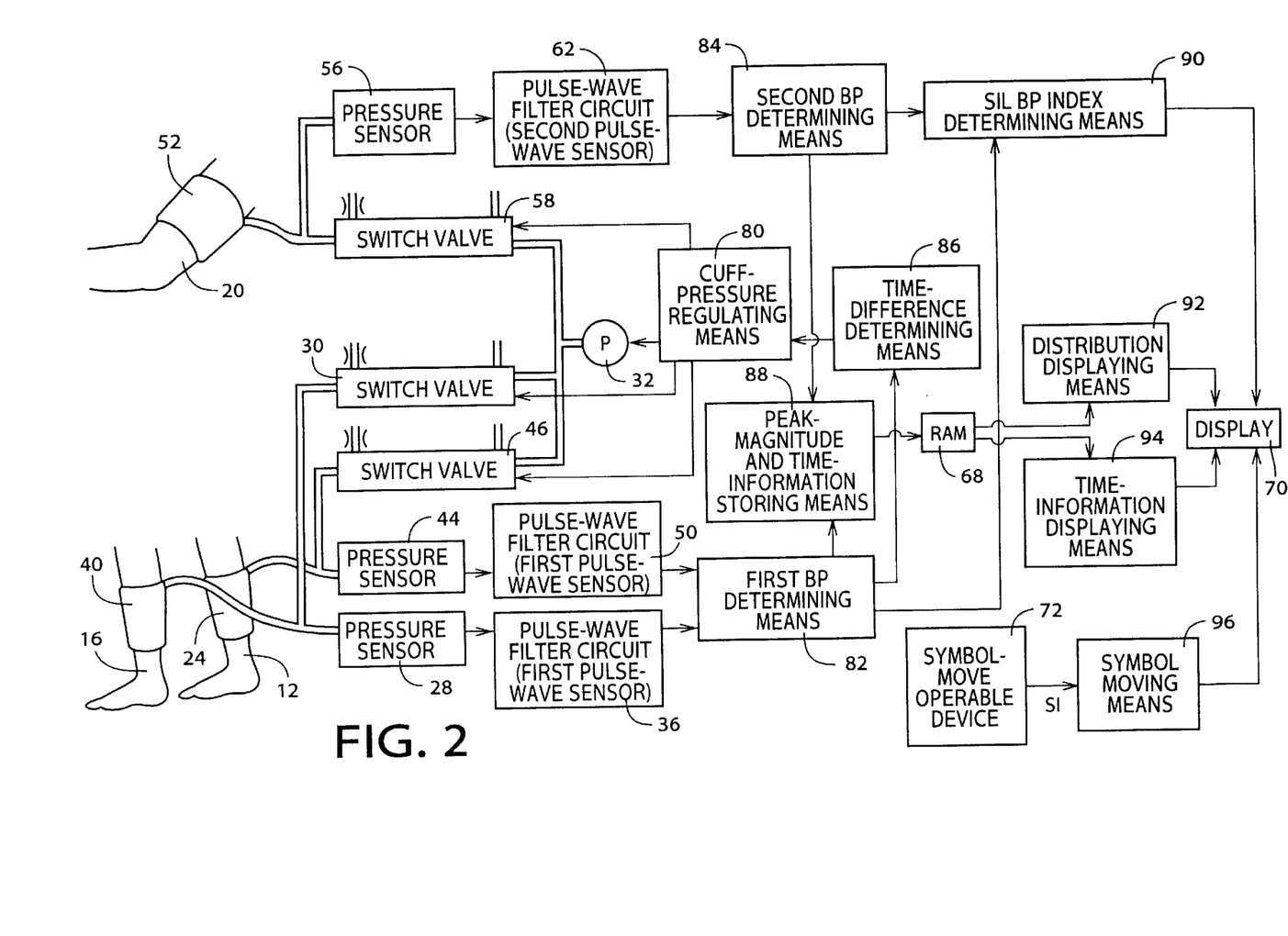
FIG. 2 is a diagrammatic view of important control functions of an electronic control device of the measuring apparatus of FIG. 1.

FIG. 2 is a diagrammatic view for explaining the important control functions of the control device 38. In an initial-time BP measuring operation, the cuff-pressure regulating means 80 controls the air pump 32, and simultaneously controls the three switch valves 30, 46, 58 that are connected to the air pump 32, so that the respective pressing pressures of the three cuffs 24, 40, 52 are quickly increased up to a predetermined target pressure value, $P_{CM}$, (e.g., about 180 mmHg) and then are slowly decreased at a rate of about 3 mmHg/sec. In a second-time BP measuring operation, the regulating means 80 controls, like the initial-time BP measuring operation, the air pump 32 and the three switch valves 30, 46, 58 connected thereto, so that the respective pressing pressures of the three cuffs 24, 40, 52 first are quickly increased up to a predetermined target pressure value $P_{CM}$ and then are slowly decreased at a rate of about 3 mmHg/sec. However, the regulating means 80 controls, based on time differences, $\Delta t_{cb}$, $\Delta t_{ca}$, determined by time-difference calculating means 86, described later, the three switch valves 30, 46, 58 to start decreasing the respective air pressures of the three cuffs 24, 40, 52 at such respective timings which should assure that a time when a right-leg first systolic BP value, $BP1_{RSYS}$, as a first systolic BP value of the right ankle 12 is measured by the right-leg first BP measuring device 14, a time when a left-leg first systolic BP value, $BP1_{LSYS}$, as a first systolic BP value of the left ankle 16 is measured by the left-leg first BP measuring device 18, and a time when a second systolic BP value, BP2, of the upper arm 20 is measured by the second BP measuring device 22, coincide with one another.

A first BP determining means 82 determines respective magnitudes (i.e., amplitudes) $P1_R$ of respective peaks of heartbeat-synchronous pulses of the right-leg first pulse wave $M1_R$ represented by the pulse-wave signal $SM_1$ obtained by the pulse-wave filter circuit 36 when the air pressure of the cuff 24 wound around the right ankle 12 is slowly decreased by the cuff-pressure regulating means 80, and determines right-leg first BP values, $BP1_R$, as BP values of the right ankle 12, according to well-known oscillometric method, based on the timewise change of the thus determined respective peak magnitudes $P1_R$. In addition, the first BP determining means 82 determines respective magnitudes (i.e., amplitudes) $P1_L$ of respective peaks of heartbeat-synchronous pulses of the left-leg first pulse wave $M1_L$ represented by the pulse-wave signal $SM_2$ obtained by the pulse-wave filter circuit 50 when the air pressure of the cuff 40 wound around the left ankle 16 is slowly decreased by the cuff-pressure regulating means 80, and determines left-leg first BP values, $BP1_L$, as BP values of the left ankle 16, according to the oscillometric method, based on the timewise change of the thus determined respective peak magnitudes $P1_L$. The right-leg first BP values $BP1_R$ include a systolic BP value $BP1_{RSYS}$ and a diastolic BP value $BP1_{RDIA}$, and the left-leg first BP values $BP1_L$ include a systolic BP value $BP1_{LSYS}$ and a diastolic BP value $BP1_{LDIA}$. Hereinafter, when it is not needed to distinguish the right-leg first BP values $BP1_R$ and the left-leg first BP values $BP1_L$ from each other, those BP values will be wholly referred to as the first BP values BP1.

A, second BP determining means 84 determines respective magnitudes (i.e., amplitudes) P2 of respective peaks of heartbeat-synchronous pulses of the second pulse wave M2 represented by the pulse-wave signal $SM_3$ obtained by the pulse-wave filter circuit 62 when the air pressure of the cuff 52 wound around the upper arm 20 is slowly decreased by the cuff-pressure regulating means 80, and determines second BP values, BP2, (systolic BP value $BP2_{SYS}$ and diastolic BP value $BP2_{DIA}$) of the upper arm 20, according to the oscillometric method, based on the timewise change of the thus determined respective peak magnitudes P2.

A time-difference determining means 86 determines, as a cuff a, one of the three cuffs 24, 40, 52 that has earliest measured, in the initial-time BP measuring operation, a BP value (i.e., one of a systolic BP value $BP_{SYS}$, a mean BP value $BP_{MEAN}$, and a diastolic BP value $BP_{DIA}$ that is used by an ankle/arm BP index determining means 90, described later), determines, as a cuff b, another of the three cuffs 24, 40, 52 that has second earliest measured a BP value, and determines, as a cuff c, the third one of the three cuffs 24, 40, 52 that has last measured a BP value. The time-difference determining means 86 additionally determines a time difference, $\Delta t_{cb}$, between a time, $t_c$, when the cuff c measured the BP value and a time, $t_b$, when the cuff b measured the BP value, and a time difference, $\Delta t_{ca}$, between the time $t_c$ and a time, $t_a$, when the cuff a measured the BP value. During the initial-time BP measuring operation, the respective instantaneous pressures of the three cuffs 24, 40, 52 continue to be equal to one another, and accordingly the BP value determined by the cuff a is the highest and the BP value determined by the cuff c is the lowest.

A peak-magnitude and time-information storing means 88 sequentially stores, in the RAM 68, the respective peak magnitudes $P1_R$, $P1_L$ of the heartbeat-synchronous pulses of each of the first pulse waves $M1_R$, $M1_L$ (i.e., the pulse-wave signals $SM_1$, $SM_2$) that are determined by the first BP determining means 82, and respective first time information representing respective first times when the heartbeat-synchronous pulses of each of the first pulse waves $M1_R$, $M1_L$ are detected by a corresponding one of the pulse-wave filter circuits 36, 50. In addition, the peak-magnitude and time-information storing means 88 sequentially stores, in the RAM 68, the respective peak magnitudes P2 of the heartbeat-synchronous pulses of the second pulse wave M2 (i.e., the pulse-wave signal $SM_3$) that are determined by the second BP determining means 84, and respective second time information representing respective second times when the heartbeat-synchronous pulses of the second pulse wave M2 are detected by the pulse-wave filter circuit 62. The first times include a time when the first BP value B P1 is measured, and the second times include a time when the second BP value B P2 is measured. Each first or second time information represents a time, t, that elapses from a reference time, e.g., a time when each BP measuring operation is started, or a time when the slow cuff deflation is started, or a parameter corresponding, one by one, to the time t. The parameter may be the instantaneous cuff pressure $P_C$ in the case where the three cuffs 24, 40, 52 are slowly deflated at the same rate.

The ankle/arm BP index determining means 90 determines or calculates an ankle/arm BP index value ("API") based on the first BP value B P1 determined by the first BP determining means 82 and the corresponding second BP value B P2 determined by the second BP determining means 88 (e.g., the systolic first BP value $BP1_{SYS}$ corresponds to the systolic second BP value $BP2_{SYS}$, and the diastolic first BP value $BP1_{DIA}$ corresponds to the diastolic second BP value $BP2_{DIA}$). For example, the API may be obtained by dividing the first BP value B P1 by the corresponding second BP value BP2, or dividing the second BP value B P2 by the corresponding second BP value BP1.

A distribution displaying means 92 displays, in a first two-dimensional graph having a time-information axis representing first time information and a first-peak-magnitude axis representing first peak magnitude, a distribution of respective first peak magnitudes P1 of heartbeat-synchronous pulses of the first pulse wave M1 detected in the second-time BP measuring operation, which magnitudes are stored in the RAM 68 by the peak-magnitude and time-information storing means 88, along the time-information axis, and additionally displays, in a second two-dimensional graph which has the time-information axis and a second-peak-magnitude axis representing second peak magnitude, a distribution of respective second peak magnitudes P2 of heartbeat-synchronous pulses of the second pulse wave M2 detected in the second-time BP measuring operation, which magnitudes are stored in the RAM 68 by the storing means 88, along the time-information axis.

A time-information displaying means 94 displays, along the time-information axis of the first two-dimensional graph in which the first distribution is displaced by the distribution displaying means 92, a first symbol representing the first time information which is stored in the RAM 68 by the peak-magnitude and time-information storing means 88 and which represents the first time when the first BP value B P1 is measured by the first BP measuring device 14 or 18, and additionally displays, along the time-information axis of the second two-dimensional graph in which the second distribution is displaced, a second symbol representing the second time information which is stored in the RAM 68 and which represents the second time when the second BP value B P2 is measured by the second BP measuring device 22. The first and second BP values are used by the ankle/arm BP index determining means 90 to determine the ankle/arm BP index value.

A symbol moving means 96 moves, based on the symbol-move signal SI supplied from the symbol-move operable device 72, one of the two symbols displayed by the time-information displaying means 94, relative to the other symbol, along the time-information axis of a corresponding one of the first and second two-dimensional graphs.

Figure 3:
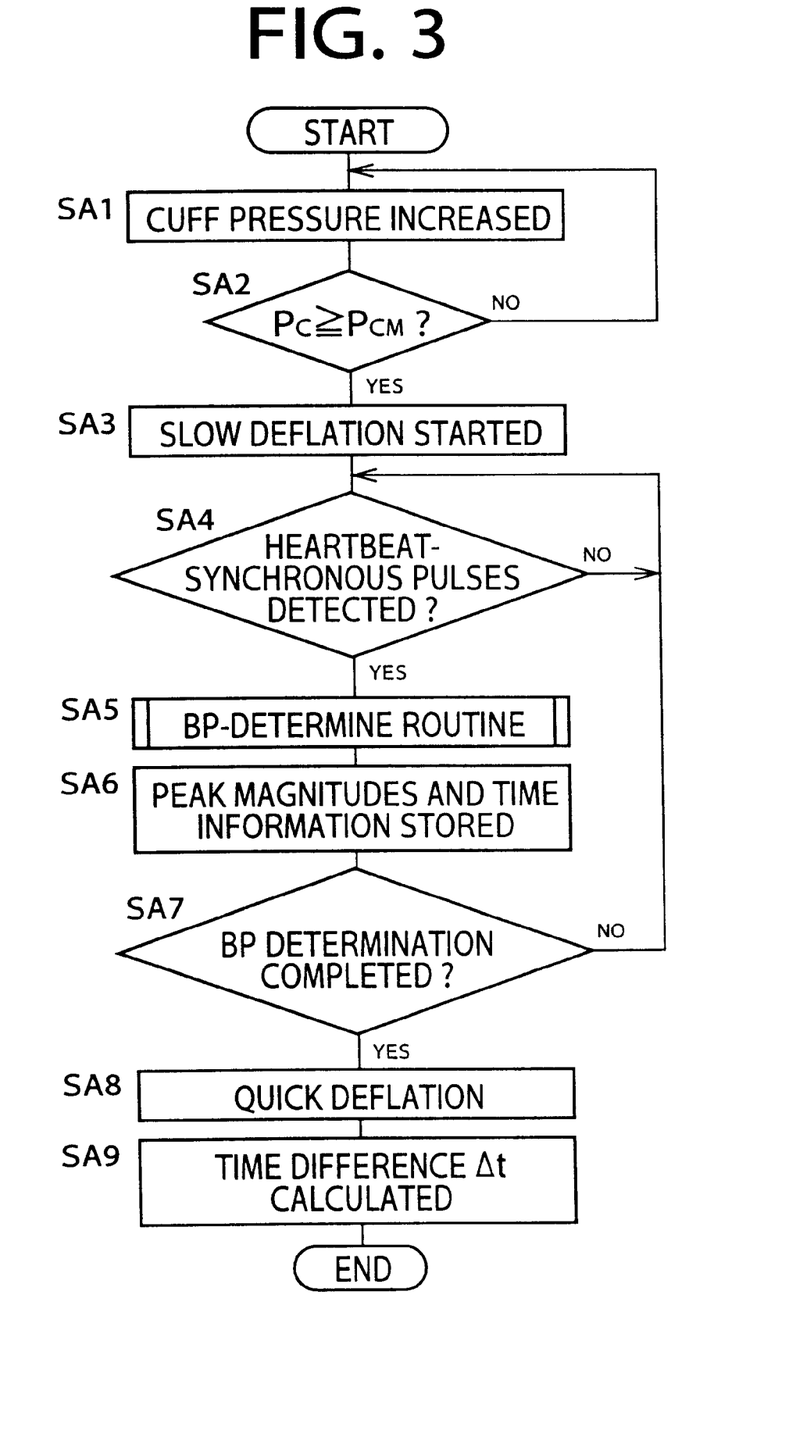
FIG. 3 is a flow chart representing an initial-time BP-measure routine according to which the control device of the measuring apparatus of FIG. 1 is operated to carry out an initial-time BP measuring operation.
Figure 4:
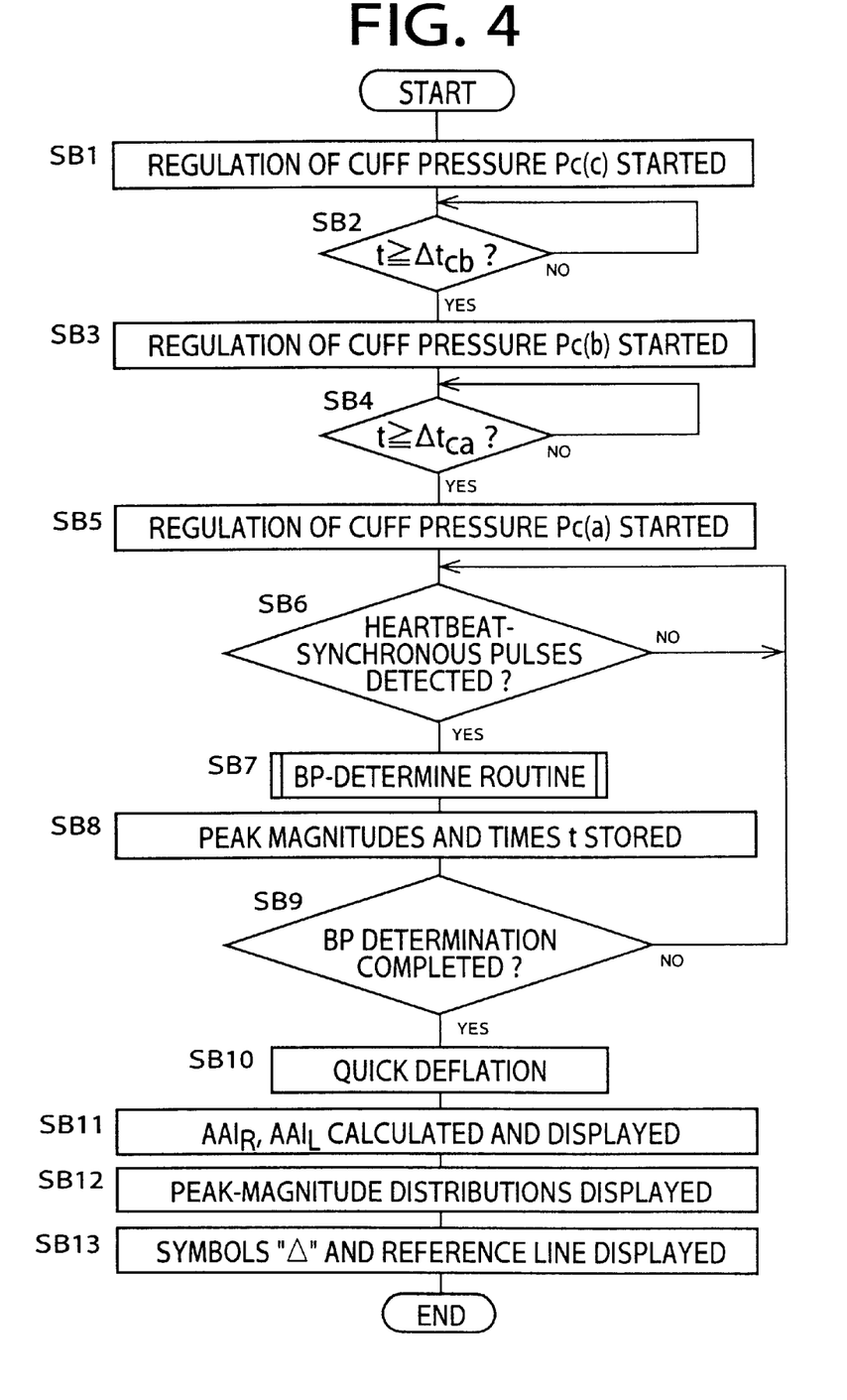
FIG. 4 is a flow chart representing a second-time BP-measure routine according to which the control device of the measuring apparatus of FIG. 1 is operated to carry out a second-time BP measuring operation.
Figure 5:
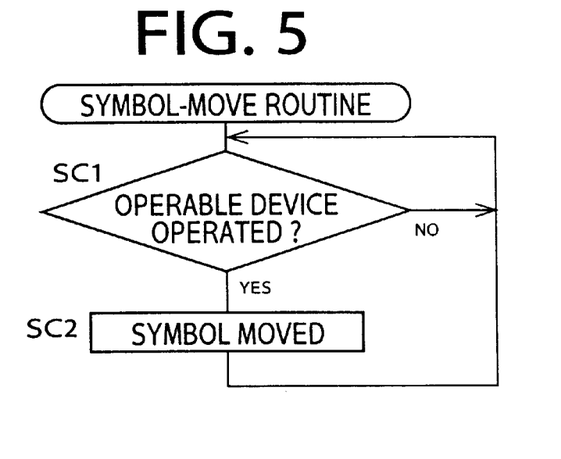
FIG. 5 is a flow chart representing a symbol-move routine according to which the control device of the measuring apparatus of FIG. 1 is operated to move a symbol displayed by a display device in the second-time BP measuring operation.

FIGS. 3, 4, and 5 are flow charts representing control programs according to which the control device 38 is operated. FIG. 3 shows the flow chart representing the initial-time BP-measure routine; FIG. 4 shows the flow chart representing the second-time BP-measure routine; and FIG. 5 shows the flow chart representing the symbol-move routine according to which one of the two symbols displayed in the second-time BP measuring operation is moved.

First, the control device 38 carries out Steps SA1, SA2, and SA3 of FIG. 3 corresponding to the cuff-pressure regulating means 80. At Step SA1, the three switch valves 30, 46, 58 are simultaneously switched to their pressure-supply positions and the air pump 32 is operated, so that the respective air pressures of the three cuffs 24, 40, 52 are quickly increased. At Step SA2, it is judged whether all the air pressures $P_C$ of the three cuffs 24, 40, 52 have reached the predetermined target pressure value $P_{CM}$ (about 180 mmHg). If a negative judgment is made at Step SA2, Steps SA1 and SA2 are repeated to continue increasing the air pressures $P_C$ of the cuffs 24, 40, 52.

If a positive judgment is made at Step SA2, the control goes to Step SA3 to stop the operation of the air pump 32 and simultaneously switch the three switch valves 30, 46, 58 to their slow-deflation positions, so that the respective: air pressures $P_C$ of the three cuffs 24, 40, 52 are decreased slowly at a predetermined low rate of about 3 mmHg/sec.

Step SA3 is followed by Step SA4 to read in the pulse-wave signals $SM_1$, $SM_2$, $SM_3$ supplied from the pulse-wave filter circuits 36, 50, 62 and judge whether the three filter circuits have detected respective one heartbeat-synchronous pulses of the three pulse waves $M1_R$, $M1_L$, M2. If a negative judgment is made at Step SA4, the control device 38 repeats Step SA4. Meanwhile, if a positive judgment is made, the control of the control device goes to the BP-determine routine of Step SA5, corresponding to the first BP determining means 82 and the second BP determining means 84. More specifically described, the control device 38 determines a magnitude $P1_R$ of a peak of the detected one heartbeat-synchronous pulse of the right-leg first pulse wave $M1_R$, a magnitude $P1_L$ of a peak of the detected one heartbeat-synchronous pulse of the left-leg first pulse wave $M1_R$, and a magnitude P2 of a peak of the detected one heartbeat-synchronous pulse of the second pulse wave M2. In addition, the control device determines a right-leg first systolic BP value $BP1_{RSYS}$, etc. based on the time-wise change of the determined peak magnitudes $P1_R$ according to a well-known oscillometric BP-determine algorithm. Similarly, the control device 38 determines a left-leg first systolic BP value $BP1_{LSYS}$, etc. based on the time-wise change of the determined peak magnitudes $P1_L$ according to the oscillometric BP-determine algorithm, and determines a second systolic BP value $BP2_{SYS}$, etc. based on the timewise change of the determined peak magnitudes P2 according to the oscillometric BP-determine algorithm. Moreover, the control device 38 stores, in the RAM 68, not only the thus determined BP values, but also respective rates of change of the cuff pressures $P_C$ of the three cuffs 24, 40, 52 connected to the three switch valves 30, 46, 58. Those rates of change of cuff pressures $P_C$ of the three cuffs 24, 40, 52 are defined by respective degrees of opening of the three switch valves 30, 46, 58, respectively.

Step SA5 is followed by Step SA6 corresponding to the peak-magnitude and time-information storing means 88. At Step SA6, the control device 38 stores, in predetermined memory areas of the RAM 68, the peak magnitudes $P1_R$, $P1_L$, P2 determined at Step SA5 for the respective one heartbeat-synchronous pulses of the pulse waves $M1_R$, $M1_L$, M2 detected at Step SA4, and respective times when the respective one heartbeat-synchronous pulses of the pulse waves $M1_R$, $M1_L$, M2 are detected.

Step SA6 is followed by Step SA7 to judge whether the three BP measuring devices 14, 18, 22 have measured or determined respective diastolic BP values at Step SA5. While a negative judgment is made at Step SA7, Steps SA4 to SA7 are repeated to determine, for respective one heartbeat-synchronous pulses of the three pulse waves $M1_R$, $M1_L$, M2, respective peak magnitudes $P1_R$, $P1_L$, P2 thereof, and repeat the BP-determine routine of Step SA5 based on the respective updated timewise changes of the peak magnitudes $P1_R$, $P1_L$, P2. In addition, the control device 38 iteratively stores the determined peak magnitudes $P1_R$, $P1_L$, P2 and the times when the heartbeat-synchronous pulses of the three pulse waves $M1_R$, $M1_L$, M2 are detected. Those times are substantially equal to respective times when the peak magnitudes $P1_R$, $P1_L$, P2 of the heartbeat-synchronous pulses of the three pulse waves $M1_R$, $M1_L$, M2 are determined.

If a positive judgment is made at Step SA7, the control of the control device 38 goes to Step SA8 corresponding to the cuff-pressure regulating means 80. At Step SA8, the three switch valves 30, 46, 58 are switched to their quick-deflation positions, so that the respective air pressures of the three cuffs 24, 40, 52 are quickly decreased.

Step SA8 is followed by Step SA9 corresponding to the time-difference determining means 86. At Step SA9, the control device 38 determines, as the cuff a, one of the three cuffs 24, 40, 52 that has earliest measured or determined the corresponding systolic BP value $BP_{SYS}$ at Step SA5, determines, as the cuff b, another of the three cuffs 24, 40, 52 that has second earliest measured the corresponding systolic BP value $BP_{SYS}$, and determines, as the cuff c, the third one of the three cuffs 24, 40, 52 that has last measured the corresponding systolic BP value $BP_{SYS}$. In addition, the control device 38 determines a time difference $\Delta t_{cb}$ between a time $t_c$ when the cuff c measured the systolic BP value $BP_{SYS}$ and a time $t_b$ when the cuff b measured the systolic BP value $BP_{SYS}$, and a time difference $\Delta t_{ca}$ between the time $t_c$ and a time $t_a$ when the cuff a measured the systolic BP value $BP_{SYS}$.

If the patient is free of the inferior-limb arterial disease, the first systolic BP value $BP1_{SYS}$ of the right or left ankle 12 or 16 will be higher than the second systolic BP value $BP1_{SYS}$ of the upper arm 20. In this case, therefore, the cuff 24 or 40 wound around the right or left ankle 12 or 16 will be determined as the cuff a, and the cuff 52 wound around the upper arm 20 will be determined as the cuff c.

After quitting from the initial-time BP-measure routine of FIG. 3, the control device 38 enters the second-time BP-measure routine of FIG. 4. The routine of FIG. 4 is started a predetermined time (e.g., 10 seconds) after the routine of FIG. 3 is ended.

First, the control device 38 carries out Steps SB1 to SB5 corresponding to the cuff-pressure regulating means 80, by starting regulating the cuff pressure $P_C$ of the cuff c that is estimated to determine last a systolic BP value $BP_{SYS}$, in the three cuffs a, b, c.

At SB1, the control device 38 starts regulating the cuff pressure $P_{C(c)}$ of the cuff c determined at Step SA9. That is, the air pump 32 is operated, and the switch valve connected to the cuff c is switched to its pressure-supply position, so that the cuff pressure $P_{C(c)}$ is increased quickly up to the predetermined target pressure value $P_{CM}$ (e.g., 180 mmHg), and subsequently the switch valve is switched to its slow-deflation position, so that the cuff pressure $P_{C(c)}$ is decreased slowly at a predetermined rate (e.g. 3 mmHg/sec). The degree of opening of the switch valve connected to the cuff c, employed in the second-time BP measuring operation, is determined according to a relationship between the degree of opening of the switch valve and the rate of change of the cuff pressure $P_{C(c)}$, stored in the RAM 68 in the initial-time BP measuring operation.

Step SB1 is followed by Step SB2 to judge whether the time t that is measured from the time when the increasing of the cuff pressure $P_{C(c)}$ is started at Step SB1, has elapsed by the time difference $\Delta t_{cb}$ determined at Step SA9. If a negative judgment is made at Step SB2, Step SB2 is repeated to continue regulating the cuff pressure $P_{C(c)}$ only.

Meanwhile, if a positive judgment is made at Step SB2, the control of the control device 38 goes to Step SB3 to start regulating the cuff pressure $P_{C(b)}$ of the cuff b, like the cuff c. That is, the switch valve connected to the cuff b is switched to its pressure-supply position, so that the cuff pressure $P_{C(b)}$ is increased quickly up to the predetermined target pressure value $P_{CM}$, and subsequently the switch valve is switched to its slow-deflation position, so that the cuff pressure $P_{C(b)}$ is decreased slowly at the same rate as that at which the cuff pressure $P_{C(c)}$ is decreased. The degree of opening of the switch valve connected to the cuff b, used in the second-time BP measuring operation, is determined based on the rate of change of the cuff pressure $P_{C(c)}$, according to a relationship between the degree of opening of the switch valve and the rate of change of the cuff pressure $P_{C(b)}$, stored in the RAM 68 in the initial-time BP measuring operation.

Step SB3 is followed by Step SB4 to judge whether the time t has elapsed by the time difference $\Delta t_{ca}$ determined at Step SA9. If a negative judgment is made at Step SB4, Step SB3 is repeated to continue regulating the cuff pressure $P_{C(c)}$ and the cuff pressure $P_{C(b)}$.

Figure 6:
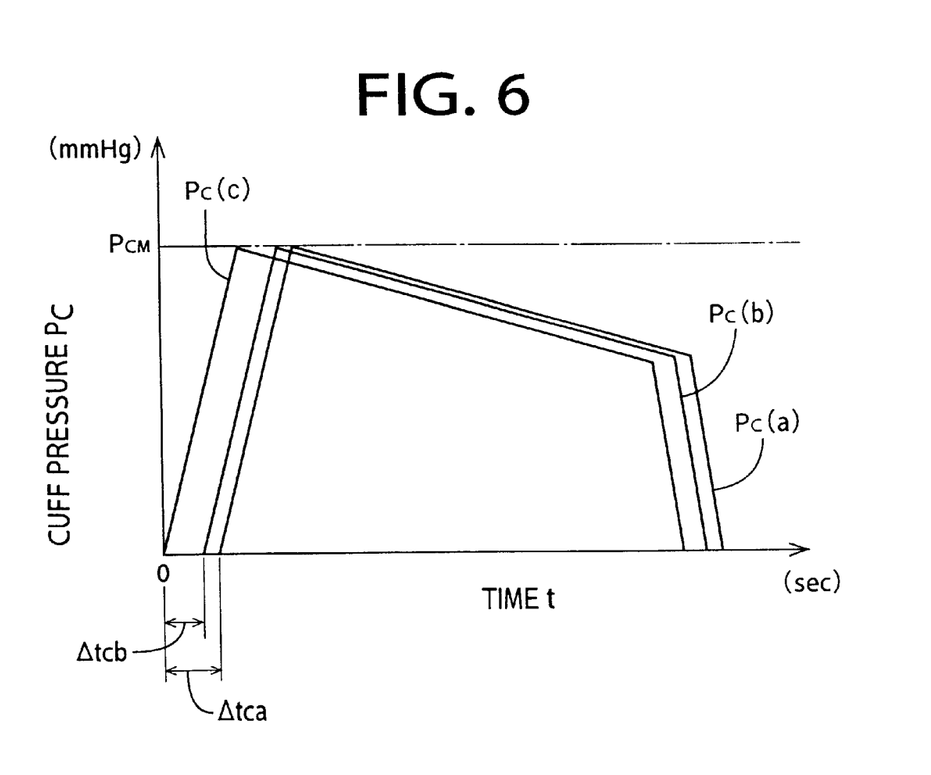
FIG. 6 is a graph showing respective changes of air pressure, $P_C$, of three inflatable cuffs of the measuring apparatus of FIG. 1, with respect to time, t, in the second-time BP measuring operation.

Meanwhile, if a positive judgment is made at Step SB4, the control goes to Step SB4 to start regulating the cuff pressure $P_{C(a)}$ of the cuff a, like the cuffs c, b. That is, the switch valve connected to the cuff a is switched to its pressure-supply position, so that the cuff pressure $P_{C(a)}$ is increased quickly up to the predetermined target pressure value $P_{CM}$, and subsequently the switch valve is switched to its slow-deflation position, so that the cuff pressure $P_{C(c)}$ is decreased slowly at the same rate as that at which the cuff pressures $P_{C(c)}$, $P_{C(b)}$ are decreased. The degree of opening of the switch valve connected to the cuff a, used in the second-time BP measuring operation, is determined based on the rate of change of the cuff pressure $P_{C(c)}$, according to a relationship between the degree of opening of the switch valve and the rate of change of the cuff pressure $P_{C(a)}$, stored in the RAM 68 in the initial-time BP measuring operation. FIG. 6 shows respective timewise changes of the three cuff pressures $P_{C(c)}$, $P_{C(b)}$, $P_{C(a)}$ that are thus regulated.

Steps SB6 to SB10 are similar to Steps SA4 to SA8 of FIG. 3. That is, at Step SB6, the control device 38 reads in the pulse-wave signals $SM_1$, $SM_2$, $SM_3$ and judge whether the control device 38 have read in respective one heartbeat-synchronous pulses of the first and second pulse waves $M1_R$, $M1_L$, M2. At Step SB7 corresponding to the first and second BP determining means 82, 84, the control device 38 determines respective peak magnitudes $P1_R$, $P1_L$, P2 of the respective one heartbeat-synchronous pulses of the first and second pulse waves $M1_R$, $M1_L$, M2, and determines a right-leg first systolic BP value $BP1_{RSYS}$, a left-leg first systolic BP value $BP1_{LSYS}$, a second systolic BP value $BP2_{SYS}$, etc., based on respective timewise changes of the three peak magnitudes $P1_R$, $P1_L$, P2, shown in FIG. 7. At Step SB8 corresponding to the peak-magnitude and time-information storing means 88, the control device 38 stores, in the predetermined memory areas of the RAM 68, the determined peak magnitudes $P1_R$, $P1_L$, P2 of the respective one heartbeat-synchronous pulses of the first and second pulse waves $M1_R$, $M1_L$, M2, and respective times t when the respective heartbeat-synchronous pulses of the first and second pulse waves $M1_R$, $M1_L$, M2 are detected, or when the peak magnitudes $P1_R$, $P1_L$, P2 of the pulses are determined. The times t include a right-leg first time $t_{1R}$ when the right-leg first systolic BP value $BP1_{RSYS}$ is measured; a left-leg first time $t_{1L}$ when the left-leg first systolic BP value $BP1_{LSYS}$ is measured; and a second time $t_2$ when the second systolic BP value $BP2_{SYS}$ is measured. At Step SB9, the control device 38 judges whether the BP determination at Step SB7 has been completed. If a positive judgment is made at Step SB9, the control goes to Step SB10 corresponding to the cuff-pressure regulating means 80, and quickly deflates the three cuffs a, b, c.

Step SB10 is followed by Step SB11 corresponding to the ankle/arm BP index determining means 90. At Step SB11, the control device 38 calculates a right ankle/arm BP index value $API1_R$ by dividing the right-leg first systolic BP value $BP1_{RSYS}$ determined at Step SB7 by the second systolic BP value $BP2_{SYS}$ determined at Step SB7, and calculates a left-leg ankle/arm BP index value $API1_L$ by dividing the left-leg first systolic BP value $BP1_{LSYS}$ determined at Step SA7 by the second systolic BP value $BP2_{SYS}$. The thus determined right-leg and left-leg ankle/arm BP index values $API1_R$, $API1_L$ are displayed in digits on the display device 70.

Figure 7:
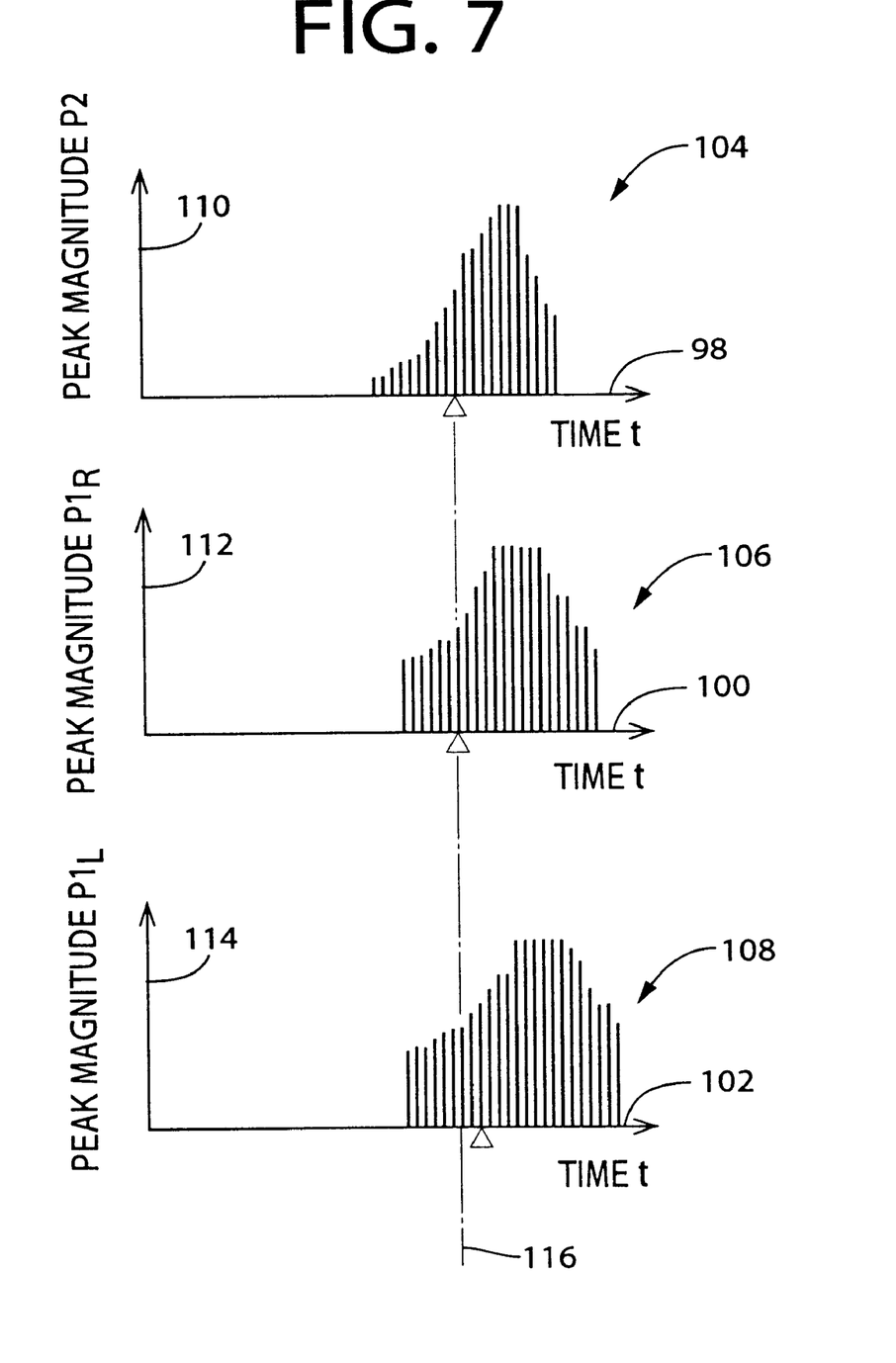
FIG. 7 is three two-dimensional graphs which are displayed by the display device of the measuring apparatus of FIG. 1 and which show a timewise distribution of respective peak magnitudes of heartbeat-synchronous pulses of a second pulse wave, a timewise distribution of respective peak magnitudes of heartbeat-synchronous pulses of a right-leg first pulse wave, and a timewise distribution of respective peak magnitudes of heartbeat-synchronous pulses of a left-leg first pulse wave, respectively.

Step SB11 is followed by Step SB12 corresponding to the distribution displaying means 92. At Step SB12, the control device 38 displays, based on the peak magnitudes $P1_R$, $P1_L$, P2 and the times t stored in the RAM 68 at Step SB8, respective distributions of the peak magnitudes $P1_R$, $P1_L$, P2 with respect to the time t, in three two-dimensional graphs 106, 108, 104 having respective time axes 100, 102, 98 each representing the time t. More specifically described, the control device 38 displays, in the fist two-dimensional graph 104 having the time axis 98 and a peak-magnitude axis 110, a distribution of the respective peak magnitudes P2 of the heartbeat-synchronous pulses of the second pulse wave M2 with respect to the time t, displays, in the second graph 106 having the time axis 100 which is parallel to the time axis 98 of the first graph 104 and has the same graduations as those of the time axis 98, and having a peak-magnitude axis 112 located on the same line as that on which the peak-magnitude axis 110 of the first graph 104 is located, a distribution of the respective peak magnitudes $P1_R$ of the heartbeat-synchronous pulses of the right-leg first pulse wave $M1_R$ with respect to the time t, and displays, in the third graph 108 having the time axis 102 which is parallel to the time axes 98, 100 and has the same graduations as those of the time axes 98, 100, and having a peak-magnitude axis 114 located on the same line as that on which the peak-magnitude axes 110, 112 are located, a distribution of the respective peak magnitudes $P1_L$ of the heartbeat-synchronous pulses of the left-leg first pulse wave $M1_L$ with respect to the time t.

Step SB12 is followed by Step SB13 corresponding to the time-information displaying means 94. At Step SB13, the control device 38 displays, in the three graphs 104, 106, 108 in which the respective peak-magnitude distributions are displayed at Step SB12, respective symbols "Δ" representing the right-leg first time $t_{1R}$, the left-leg first time $t_{1L}$, and the second time $t_2$ that had been stored at Step SB8, as shown in FIG. 7. In addition, the display device 70 displays a reference line 116 which passes through one of the three symbols "Δ" (e.g., the symbol representing the second time $t_2$, as shown in FIG. 7) and is parallel to the three peak-magnitude axes 110, 112, 114. This reference line 116 is for helping an observer easily recognize the time differences among the first and second times $t_{1R}$, $t_{1L}$, $t_2$.

In the present embodiment, the control device 38 determines, based on the results obtained in the initial-time BP determining operation, the respective timings at which the respective regulations of cuff pressures $P_C$ of the three cuffs 24, 40, 52 are started, so that, in the second-time BP measuring operation, the three BP measuring devices 14, 18, 22 simultaneously measure or determine respective systolic BP values $BP1_{RSYS}$, $BP1_{LSYS}$, $BP2_{SYS}$. However, the three graphs 104, 106, 108 shown in FIG. 7 indicate that the left-leg first systolic BP value $BP1_{LSYS}$ was measured several pulses after the right-leg first and second systolic BP values, $BP1_{RSYS}$, $BP2_{SYS}$ were measured. In addition, the observer can judge, from respective tendencies of change of the three peak-magnitude distributions at respective positions indicated by the three symbols "Δ", whether the three systolic BP values $BP1_{RSYS}$, $BP1_{LSYS}$, $BP2_{SYS}$ have been properly measured.

Then, the control device 38 carries out the symbol-move routine of FIG. 5. First, at Step SC1, the control device 38 judges whether the control device 38 has received the symbol-move signal SI from the symbol-move operable device 72. If a negative judgment is made at this step, Step SC1 is repeated. Meanwhile, when the operable device 72 is operated and the control device 38 receives the signal SI from the operable device 72, a positive judgment is made at Step SC1. Then, the control of the control device 38 goes to Step SC2 corresponding to the symbol moving means 96. At Step SC2, the control device 38 moves, along the time axes 100, 102, the respective distributions of the peak magnitudes $P1_R$, $P1_L$ of the two first pulse waves $M1_R$, $M1_L$ and the two symbols "Δ" representing the two first times $t_{1R}$, $t_{1L}$, by an amount or distance corresponding to the amount or length of the symbol-move signal SI.

As is apparent from the foregoing description, the peak-magnitude and time-information storing means 88 (SB8) stores, in the RAM 68, the respective peak magnitudes $P1_R$, $P1_L$ of the heartbeat-synchronous pulses of each of the first pulse waves $M1_R$, $M1_L$ detected by the pulse-wave filter circuits 36, 50, and the respective times t when the heartbeat-synchronous pulses of each of the first pulse waves $M1_R$, $M1_L$ are detected by a corresponding one of the pulse-wave filter circuits 36, 50, and additionally stores, in the RAM 68, the respective peak magnitudes P2 of the heartbeat-synchronous pulses of the second pulse wave M2 detected by the pulse-wave filter circuit 62, and the respective times t when the heartbeat-synchronous pulses of the second pulse wave M2 are detected by the pulse-wave filter circuit 62. The distribution displaying means 92 (SB12) displays, based on the peak magnitudes $P1_R$, $P1_L$, P2 and the respective times t stored in the ROM 68, the respective distributions of the peak magnitudes $P1_R$, $P1_L$, P2 of the first and second pulse waves $M1_R$, $M1_L$, M2, each with respect to the time t, in the respective two-dimensional graphs 104, 106, 108 having the respective time axes 98, 100, 102 and the respective peak-magnitude axes 110, 112, 114. The time-information displaying means 94 (SB13) displays, in the graphs 104, 106, 108, the respective symbols representing the respective times t when the respective BP values $BP1_{RSYS}$, $BP1_{LSYS}$, $BP2_{SYS}$ are measured. Therefore, the observer can easily recognize visually the time differences among the respective times t when the respective BP values $BP1_{RSYS}$, $BP1_{LSYS}$, $BP2_{SYS}$ are measured.

In addition, in the present embodiment, the observer or the operator can move, along the time axis 102, the symbol representing the first time t when the left-leg first systolic BP value $BP1_{LSYS}$ is measured, to a position corresponding to a position where the symbol representing the second time t when the second systolic BP value $BP2_{SYS}$ is measured, is indicated along the time axis 98. Judging from the amount of operation of the operable device 72 needed to cause the two symbols to be aligned with each other with respect to the time t, the observer can easily recognize the time difference between the first time when the first BP value $BP1_{LSYS}$ is measured and the second time when the second BP value $BP2_{SYS}$ is measured.

While the present invention has been described in its preferred embodiment, it may be otherwise embodied.

For example, in the illustrated embodiment, the time-information displaying means 94 (SB13) displays, in the two-dimensional graphs 104, 106, 108 in which the respective distributions of the peak magnitudes $P1_R$, $P1_L$, P2 are indicated, the respective symbols "Δ" representing the right-leg and left-leg first times $t_{1R}$, $t_{1L}$ and the second time $t_2$. However, the time-information displaying means 94 may be so modified as to display, on a one-dimensional graph having a time axis only, respective symbols representing the right-leg and left-leg first times $t_{1R}$, $t_{1L}$ and the second time $t_2$.

In the illustrated embodiment, the symbols "Δ" representing the right-leg and left-leg first times $t_{1R}$, $t_{1L}$ and the second time $t_2$, may be replaced with other sorts of symbols, such as "●" (black circles).

In the illustrated embodiment, in the three two-dimensional graphs 104, 106, 108, the respective distributions of the peak magnitudes $P1_R$, $P1_L$, P2 of the first and second pulse waves $M1_R$, $M1_L$, M2 are indicated. However, it is possible to indicate, in a single two-dimensional graph, the respective distributions of the peak magnitudes $P1_R$, $P1_L$, P2 of the first and second pulse waves $M1_R$, $M1_L$, M2. In this case, three symbols representing the respective times t when the three BP values are measured by the three BP measuring devices 14, 18, 22, are displayed in different colors or shapes which are easily distinguishable from one another.

In the illustrated embodiment, the ankle/arm BP index measuring device 10 carries out the initial-time and second-time BP measuring operations on each of the right and left ankles 12, 16 and the upper arm 20 of the patient. However, the measuring device 10 may be so modified as to carry out a single BP measuring operation on each body portion of the patient.

In the illustrated embodiment, each of the right-leg first BP measuring device 14, the left-leg first BP measuring device 16, and the second BP measuring device 22 measures a BP value according to the oscillometric method. However, each of the three BP measuring devices 14, 16, 22 may be one which measures a BP value according to a well-known Korotkoff-sound method in which a BP value is measured based on a cuff-pressure value read at a time when Korotkoff sounds are first or last detected. Otherwise, each device 14, 16, 22 may be one which measures a BP value according to a supersonic Doppler method in which, while a pressure which presses an artery is changed, a supersound emitter and a supersound receiver which are provided right above the artery cooperate with each other to detect the opening and closing of the artery.

Although in the illustrated embodiment the right-leg first BP value $BP1_R$ and the left-leg first BP value $BP1_L$ are measured from the right and left ankles 12, 16 of the patient, respectively, it is possible to measure only one of the two first BP values $BP1_R$, $BP1_L$.

The ankle/arm BP index measuring apparatus 10 is a sort of inferior-and-superior-limb BP index measuring apparatus wherein an ankle is selected as an inferior limb and an upper arm is selected as a superior limb. However, a femoral portion or a toe may be selected as an inferior limb, and a wrist or a finger may be selected as a superior limb.

It is to be understood that the present invention may be embodied with other changes, improvements, and modifications that may occur to a person skilled in the art without departing from the scope and spirit of the invention defined in the appended claims.

What is claimed is:

1. An apparatus for measuring a superior-and-inferior-limb blood-pressure index of a living subject, comprising:

a first blood-pressure measuring device which measures a first blood pressure of an inferior limb of the subject;

a second blood-pressure measuring device which measures a second blood pressure of a superior limb of the subject;

index determining means for determining the superior-and-inferior-limb blood-pressure index, based on the first blood pressure measured by the first blood-pressure measuring device and the second blood pressure measured by the second blood-pressure measuring device;

a time-information storing device which stores first time information representing a first time when the first blood pressure is measured by the first blood-pressure measuring device, and second time information representing a second time when the second blood pressure is measured by the second blood-pressure measuring device; and a time-information displaying device which displays, in a graph having at least a time-information axis representing time information, a first symbol representing the first time information stored in the time-information storing device, and a second symbol representing the second time information stored in the time-information storing device, along the time-information axis, so that an observer can compare the first and second symbols with each other.

2. An apparatus according to claim 1, wherein the time-information storing device comprises a memory which temporarily stores the first time information and the second time information.

3. An apparatus according to claim 2, wherein the memory comprises a random access memory.

4. An apparatus according to claim 1, further comprising:

an operable device which is operable by an operator and which outputs a symbol-move signal representing an amount of operation thereof; and symbol moving means for moving, based on the symbol-move signal supplied from the operable device, one of the first and second symbols relative to the other of the first and second symbols, along the time-information axis of the graph.

5. An apparatus according to claim 1, wherein the index determining means comprises means for determining, as the superior-and-inferior-limb blood-pressure index, a ratio of the first blood pressure to the second blood pressure, or a ratio of the second blood pressure to the first blood pressure.

6. An apparatus for measuring a superior-and-inferior-limb blood-pressure index of a living subject, comprising:

a first blood-pressure measuring device which includes a first inflatable cuff which is adapted to be wound around an inferior limb of the subject, and a first pulse-wave sensor which detects each of a plurality of heartbeat-synchronous pulses of a first pulse wave produced from a first artery pressed by the first cuff, the first blood-pressure measuring device measuring a first blood pressure of the inferior limb of the subject;

a second blood-pressure measuring device which includes a second inflatable cuff which is adapted to be wound around a superior limb of the subject, and a second pulse-wave sensor which detects each of a plurality of heartbeat-synchronous pulses of a second pulse wave produced from a second artery pressed by the second cuff, the second blood-pressure measuring device measuring a second blood pressure of the superior limb of the subject;

index determining means for determining the superior-and-inferior-limb blood-pressure index, based on the first blood pressure measured by the first blood-pressure measuring device and the second blood pressure measured by the second blood-pressure measuring device;

a peak-magnitude and time-information storing device which stores a first magnitude of a peak of each of the heartbeat-synchronous pulses of the first pulse wave detected by the first pulse-wave sensor, and a first time information representing a first time when said each pulse of the first pulse wave is detected by the first pulse-wave sensor, and stores a second magnitude of a peak of each of the heartbeat-synchronous pulses of the second pulse wave detected by the second pulse-wave sensor, and a second time information representing a second time when said each pulse of the second pulse wave is detected by the second pulse-wave sensor;

a distribution displaying device which displays, in a first two-dimensional graph having a time-information axis representing time information and a first-peak-magnitude axis representing first peak magnitude, a distribution of the respective first peak magnitudes of the heartbeat-synchronous pulses of the first pulse wave, stored in the peak-magnitude and time-information storing device, along the time-information axis, and additionally displays, in a second two-dimensional graph which has the time-information axis and a second-peak-magnitude axis representing second peak magnitude, a distribution of the respective second peak magnitudes of the heartbeat-synchronous pulses of the second pulse wave, stored in the peak-magnitude and time-information storing device, along the time-information axis; and a time-information displaying device which displays, along the time-information axis of the first two-dimensional graph in which the first distribution is displaced, a first symbol representing the first time information, which is stored in the peak-magnitude and time-information storing device and which represents the first time when the first blood pressure is measured by the first blood-pressure measuring device, and additionally displays, along the time-information axis of the second two-dimensional graph in which the second distribution is displaced, a second symbol representing the second time information which is stored in the peak-magnitude and time-information storing device and which represents the second time when the second blood pressure is measured by the second blood-pressure measuring device.

7. An apparatus according to claim 6, wherein the peak-magnitude and time-information storing device comprises a memory which temporarily stores the respective first peak magnitudes of the heartbeat-synchronous pulses of the first pulse wave, the respective first time information representing the respective first times when the respective heartbeat-synchronous pulses of the first pulse wave are detected by the first pulse-wave sensor, the respective second peak magnitudes of the heartbeat-synchronous pulses of the second pulse wave, and the respective second time information representing the respective second times when the respective heartbeat-synchronous pulses of the second pulse wave are detected by the second pulse-wave sensor.

8. An apparatus according to claim 7, wherein the memory comprises a random access memory.

9. An apparatus according to claim 6, further comprising:

an operable device which is operable by an operator and which outputs a symbol-move signal representing an amount of operation thereof; and symbol moving means for moving, based on the symbol-move signal supplied from the operable device, one of the first and second symbols relative to the other of the first and second symbols, along the time-information axis of a corresponding one of the first and second two-dimensional graphs.

10. An apparatus according to claim 6, wherein the index determining means comprises means for determining, as the superior-and-inferior-limb blood-pressure index, a ratio of the first blood pressure to the second blood pressure, or a ratio of the second blood pressure to the first blood pressure.

* * * * *